(12) United States Patent
Fevola et al.

(10) Patent No.: US 10,383,804 B1
(45) Date of Patent: Aug. 20, 2019

(54) METHOD OF USING CLEANSING COMPOSITION THAT IMPROVES TOUCH BETWEEN CAREGIVER AND CHILD

(71) Applicant: Johnson & Johnson Consumer Inc., Skillman, NJ (US)

(72) Inventors: Michael J. Fevola, Belle Mead, NJ (US); Christina Irene Lee, Plainsboro, NJ (US); Janeta Nikolovski, Princeton, NJ (US); Katie Rotella, New Bruswick, NJ (US); Russel M. Walters, Philadelphia, PA (US); Christina Bishop, Clifton, NJ (US); Marni Dexter, Cranford, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

(21) Appl. No.: 15/968,158

(22) Filed: May 1, 2018

Related U.S. Application Data

(60) Provisional application No. 62/501,222, filed on May 4, 2017.

(51) Int. Cl.
| | | |
|---|---|---|
| *A61K 8/19* | (2006.01) | |
| *A61K 8/368* | (2006.01) | |
| *A61K 8/44* | (2006.01) | |
| *A61Q 19/10* | (2006.01) | |
| *A61K 8/60* | (2006.01) | |
| *A61K 8/81* | (2006.01) | |
| *A61K 8/49* | (2006.01) | |
| *A61K 8/34* | (2006.01) | |
| *A61K 8/73* | (2006.01) | |

(52) U.S. Cl.
CPC ............ *A61K 8/442* (2013.01); *A61K 8/19* (2013.01); *A61K 8/345* (2013.01); *A61K 8/368* (2013.01); *A61K 8/44* (2013.01); *A61K 8/4973* (2013.01); *A61K 8/602* (2013.01); *A61K 8/731* (2013.01); *A61K 8/8152* (2013.01); *A61Q 19/10* (2013.01)

(58) Field of Classification Search
CPC .................................................... A61K 8/442
USPC ........................................................ 514/183
See application file for complete search history.

(56) References Cited

U.S. PATENT DOCUMENTS

| | | | | |
|---|---|---|---|---|
| 5,720,961 A | * | 2/1998 | Fowler | A61Q 5/02 424/401 |
| 2009/0181873 A1 | * | 7/2009 | Ryklin | A61K 8/39 510/123 |
| 2018/0318195 A1 | * | 11/2018 | Blachechen | A61K 8/44 |

OTHER PUBLICATIONS

Glycerin in Trianon Dry Skin Cream sold in 1937. (Year: 1937).*

* cited by examiner

*Primary Examiner* — Yong L Chu
(74) *Attorney, Agent, or Firm* — Laura A. Donnelly

(57) ABSTRACT

Compositions and methods for improving the experience of bath time that promotes good skin-to-skin contact between caregiver and child are disclosed.

1 Claim, 2 Drawing Sheets

METHOD OF USING CLEANSING COMPOSITION THAT IMPROVES TOUCH BETWEEN CAREGIVER AND CHILD

This application claims priority of the benefit of the filing of U.S. Provisional Application Ser. No. 62/501,222, filed May 4, 2017, the contents of which are hereby incorporated by reference in their entirety.

FIELD OF THE INVENTION

The present invention relates to a product and method that improves the experience of bathing a child. The invention includes products and methods that increase enjoyment during bath, while promoting the length and frequency of baths. This is particularly beneficial in encouraging a caregiver to bathe a child.

BACKGROUND

Cleansing products, such as washes and soaps, are used to clean the skin, including the use of such products on the skin of children and babies. In such instances, a caregiver, such as a parent or guardian, may apply cleansing products onto the child's skin during a bath. Today, cleansers are typically designed not only to cleanse the skin but also to provide moisture to the skin of the child.

However, it has now been discovered that the frequency of bathing is decreasing for a number of reasons. For example, it takes time to engage in a bath for the child, and some caregivers may not wish to take the time to bathe the child regularly. Further, the experience of bathing typically is not an enjoyable experience, and many caregivers focus on the "functional" aspects of bathing, such as wetting skin, applying cleanser, and washing skin. Other caregivers worry that over-bathing may dry the skin of the child.

The present inventors have discovered that the non-functional aspects of bathing are critical to development of the child, including social, cognitive and psychological developments and improving bonding between the child and the caregiver. Such non-functional aspects include eye contact, skin-to-skin touch, and overall happiness and play time during the bath. Of particular importance is the sensation the child feels on its skin, as young children, particularly babies, are dependent upon touch to explore the world.

It is therefore a desire to provide a product and method that improves the experience of the bath, and promotes the frequency and pleasure during bath time, including the reduction of "functional" aspects and increase in "non-functional" aspects of bath.

DETAILED DESCRIPTION

Figure 1:
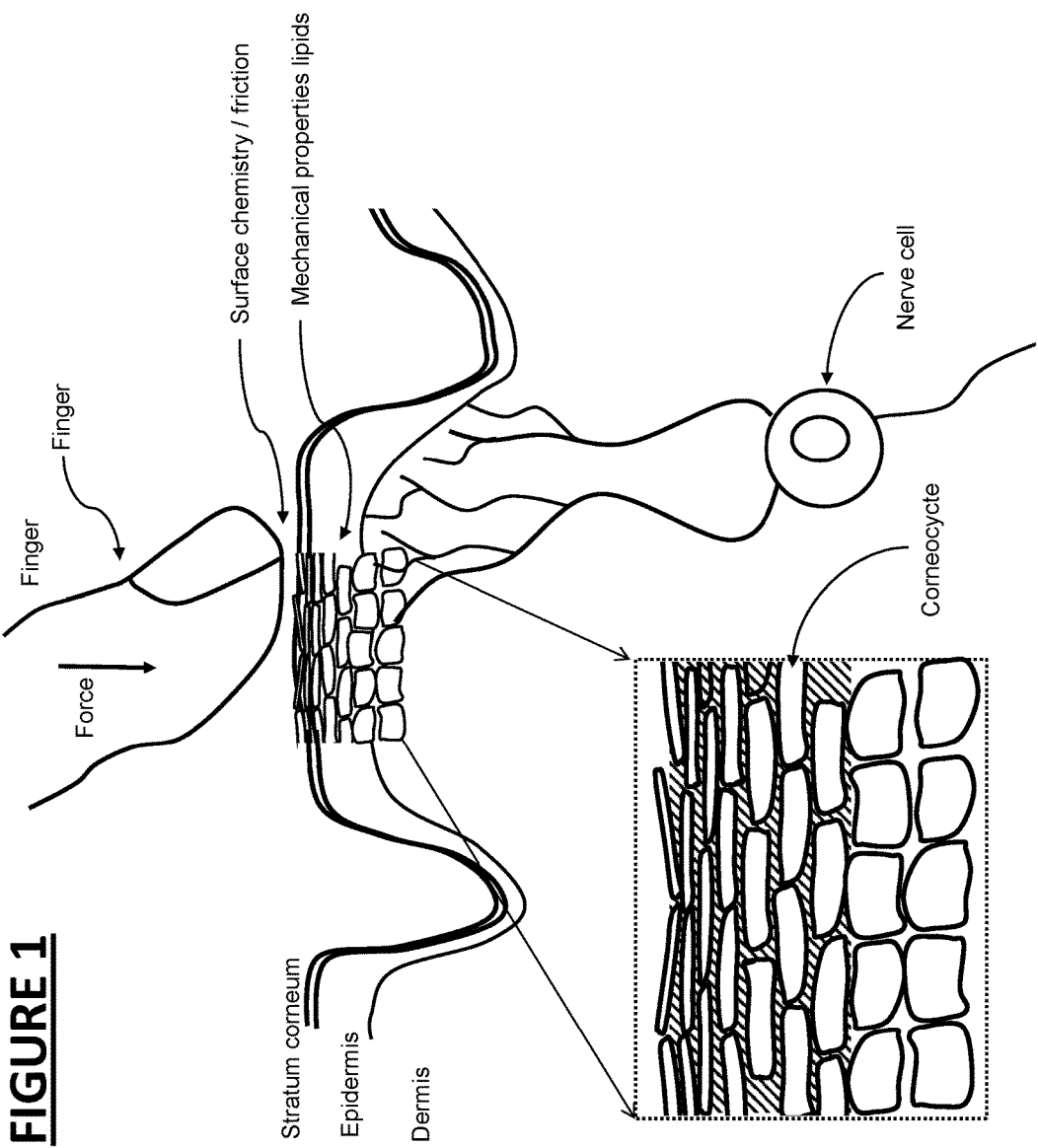
FIG. 1 shows the surface of the skin, including the stratum corneum and the dermis.

As used herein, a "cleanser" is a product applied to the skin of a user to cleanse the skin, and includes soaps, washes, and other similar products. As used herein, a "bath" (or "bathing") refers to the steps of cleansing the skin of a user and may include the presence of water or may be in a water-free environment. As used herein, the term "child" includes a human ranging in age from newborn through age 8, and expressly encompasses babies, toddlers, and other children who may need assistance during a bath. As used herein, the term "caregiver" includes any person that bathes a child, and may include a parent, guardian, or other individual bathing a child. The present invention will describe and discuss a caregiver bathing a child, but it is to be understood that the invention may relate to any person bathing a second person.

As noted above, the frequency of baths is decreasing, but the benefits associated with bath time are important. While the functional aspects of bath time, such as the act of cleansing the skin, are helpful, the present invention focuses on the non-functional aspects of bath time. Bathing is an especially important time for direct skin to skin touch between care giver and child. During bathing, the child is typically not wearing any clothing so that all the child's skin is directly exposed. For example, the skin-to-skin contact between caregiver and child improves bonding and happiness. In particular, the caregiver's fingers touching the dermis of a child activates neurons within the child, and therefore improves and increases happiness and enjoyment. Other non-functional aspects of bathing include eye contact, smiling, laughing, playing, and general enjoyment.

While the functional aspects of bathing are important, it has been discovered that cleansers can affect skin mechanics and the transfer of touch from the caregiver to the skin of the child. For example, surfactants are known to affect skin in that they remove lipids, and alter skin lipid order. This results in a decrease in the skin barrier and an increase in the water flux out of the skin. These results can impact the mechanical properties of the skin. Further, altering the surface chemistry results in a changing of the friction of an object sliding across the skin (e.g., the fingers of a caregiver sliding across the child skin). Finally, common cleansers add a film onto the skin, in the format of a skin barrier fortifying agent. This skin barrier fortifying agent may serve to protect the skin, but block the direct skin-to-skin contact. Such fortifying agents include, for example, plant oils (ex. soybean oil, sunflower seed oil, coconut oil) and mineral oil.

The present invention is beneficial in that it provides a cleanser and/or a method of cleansing that promotes the ideal skin-to-skin contact between caregiver and child. The cleanser or cleansing apparatus includes a formulation that is mild and has minimal effects on the skin, such as described above with respect to surfactants. The cleanser or cleansing apparatus desirably provides good rinsability and low resulting residue during and after the bath. The desirable cleanser further avoids the use of components such as sulfates.

Improved Skin-to-Skin Contact

The skin of humans is made of several layers, including the stratum corneum (the outermost layer), the epidermis, and the dermis. The stratum corneum includes a number of components, including, for example, cholesterol, fatty acids, and ceramides. The stratum corneum is thin and stiff, comprised of dead anucleated corneocytes with highly order lipids between the corneocytes. The corneocytes are highly crosslinked by corneodesmosomes and the stratum corneum lipid is highly organized, leading to a still stratum corneum. The stratum corneum is connected to a softer and thicker dermis. This mismatch between a thick stiff layer on top of a soft thicker layer likely leads to wrinkling and bunching instabilities. As the stratum corneum is exposed to the external environment is can be altered by topically applied substances.

Nerves are located within the skin of the human, as seen in FIG. 1 attached to this application. C fibers are one class of nerve fibers found in the skin and are part of the somatosensory system. These afferent nerve fibers are activated by external stimuli and convey signals from the periphery to the central nervous system. There are several types of c fibers. For example, the stimulation of c-tactile fibers provides a perception of pleasantness and soothing to a specific type of low velocity and/or low force touch, typical of a caress.

FIG. 1 shows the surface of the skin, including the stratum corneum and the dermis. As can be seen, the skin to be touched is not an even, flat surface, but rather includes ridges and valleys. The caregiver touches (e.g., with his or her finger, as seen in FIG. 1). There are various mechanics of touch, which depend upon various factors, including the force applied (stress/strain); the area of contact between the finger and the skin; the friction of the touching member (such as a finger or hand) and the skin to be touched, which includes topography and surface chemistry; the mechanical properties within the skin which depend on the lipid order of the stratum corneum; and the water content of the skin touched and the touching skin. Cleansers and lotions can affect these factors in a number of different ways, each of which may impact the touch on the skin.

The transmission of the mechanical properties from the finger of the toucher (e.g., a caregiver) through the skin of the person being touched (e.g., a child) depends on the friction between the finger and the skin and then the mechanical properties of the skin. The friction is influenced by the surface topography and surface chemistry of the two interfaces. Many conventional personal care products can deposit a film on the skin surface. This film, typically including skin conditioning agents, can also mediate the mechanical forces of touch and change the friction between the two surfaces. The present invention seeks to provide a cleanser and cleansing method that limits the formation of a film on the skin, thereby improving touch between the finger or skin of the caregiver and the skin of the child.

Figure 2:
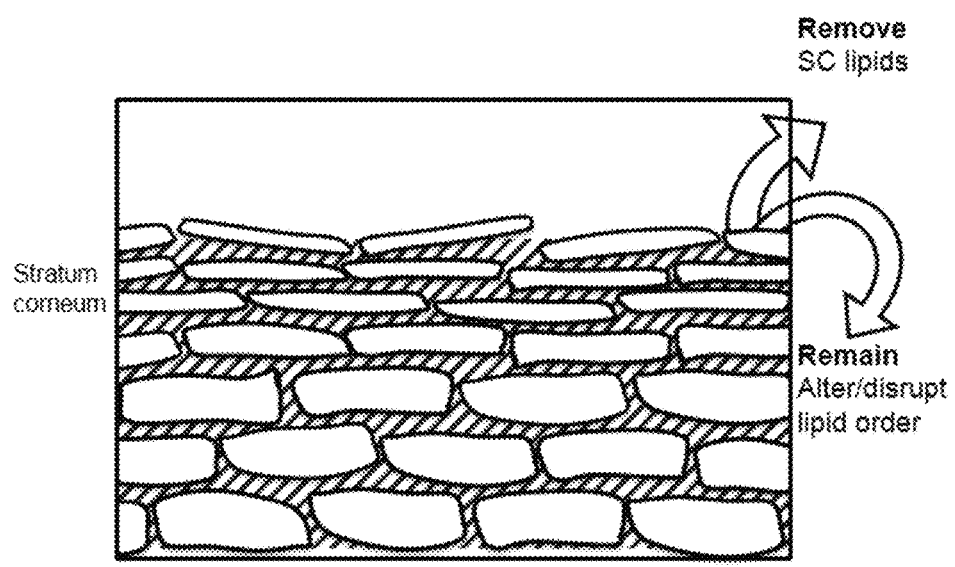
FIG. 2 shows how surfactant in a cleanser can affect the skin.

Cleansers include surfactants to achieve cleansing of the body and hair. The Surfactant in a cleanser can affect the skin in a number of ways, all of which alter the mechanical properties of the skin and thereby affect how touch is transmitted through the skin to the nerves in the skin. See FIG. 2.

Cleansers can solubilize and remove Stratum Corneum lipids, taking stratum corneum lipids out of the stratum corneum and into the water phase to be rinsed away. More importantly surfactant from cleansers can also remain in the stratum corneum and interaction with stratum corneum lipids. It has been shown that surfactant that enters and remains in the skin likely exists within the stratum corneum lipids and alters skin lipid order. Surfactant in the stratum corneum lipids results in less ordered stratum corneum lipids. The mechanical properties of the stratum corneum lipids (ex. loss modulus and storage modulus) are determined by the molecular order of the stratum corneum lipids ("SC lipids"). SC lipids that are less ordered, or less crystalline, have different mechanical properties than more order stratum corneum lipids. Less ordered stratum corneum lipids tend to be more compliant or less stiff and less solids.

Most of the barrier to transport in the stratum corneum is due to the highly organized stratum corneum lipids. The reduction in lipids order that can be caused by aggressive surfactant also leads to a decrease in skin barrier and an increase in water flux out of the skin. The corneocytes in the stratum corneum can swell significantly with water and the modulus of the corneocytes is highly dependent on the water content of the corneocytes. A decrease in skin barrier and a corresponding increase in water flux out of the skin leads to a reduction in the water content in the corneocytes. All of these effect the mechanical properties of the skin Mild cleansing that does not disrupt the skin barrier is especially important in infants and young children. The skin barrier of infants is not fully formed and still developing over the first four or five years of life. Infants have a thinner stratum corneum than adults and much higher level of water loss their skin.

In addition to surfactants, typical cleansers contain conditioning agents such as polyquaternium 10, polyquaternium 51 that alter the surface chemistry of the skin. Altering the surface chemistry results in a change in the friction of an object sliding across the skin. The change in friction therefore affects the transmission of touch.

Further, typical cleansers contain skin barrier fortifying agents such as plant oils (ex. soybean oil, sunflower seed oil, coconut oil, mineral oil). This is commonly added to a cleanser to provide enhanced barrier for water transport out of the skin.

Moisturizing oils, which are exogenous agents, added on top of the skin may form an additional exogenous (unnatural) layer on top of the skin. This additional layer also effects the mechanical transduction of forces from the finger to the neurons below and within the skin.

With the foregoing in mind, the cleansers of the present invention desirably avoid the impact of transmission of touch between caregiver and child's skin to the extent possible. While the cleansers should include beneficial agents, it is particularly desirable that the cleansers of the present invention avoid including, or only use slight levels of lipophilic skin condition molecules, for example, di-PPG-2 myreth-10 adipate. It is desirable that the cleansers of the present invention also avoid silicones or siloxanes, such as polydimethylsiloxane, polydimethylcyclosiloxane, hexamethyldisiloxane, cyclomethicone fluids such as polydimethylcyclosiloxane available commercially from Dow Corning Corporation of Midland, Mich. under the tradename, "DC-345" and mixtures thereof, and cyclomethicone fluids.

The cleansing compositions of the present invention desirably include no more than about 2% of the active materials having an HLB less than 8, and no more than about 1% of the active materials having an HLB less than 6. In addition, the cleansing compositions of the present invention desirably include no more than about 2% of the active material having a carbon chain longer than C16, and no more than about 1% of the active material having a carbon chain longer than C18.

It is desired that the cleansing composition include a low level of conditioning agents, such as less than about 1%, or less than about 0.5%, or less than about 0.1% by weight of the composition.

The cleansers of the present invention desirably also avoid the use of harsh surfactants, such as sulfates, including alkyl sulfates and alkyl ether sulfates.

The cleansers of the present invention either do not contain or contain less than 1% by weight of the composition of a cationic surfactant, including, for example, alkyl quaternaries (mono, di, or tri), benzyl quaternaries, ester quaternaries, ethoxylated quaternaries, alkyl amines, and mixtures thereof, wherein the alkyl group has from about 6 carbon atoms to about 30 carbon atoms.

It is desired that the cleansers of the present invention include one or more non-ionic surfactants, such as PEG-80 SL. Other examples of suitable nonionic surfactants include, but are not limited to, fatty alcohol acid or amide ethoxylates, monoglyceride ethoxylates, sorbitan ester ethoxylates alkyl polyglycosides, mixtures thereof, and the like. Certain preferred nonionic surfactants include polyoxyethylene derivatives of polyol esters, wherein the polyoxyethylene derivative of polyol ester (1) is derived from (a) a fatty acid containing from about 8 to about 22, and preferably from about 10 to about 14 carbon atoms, and (b) a polyol selected from sorbitol, sorbitan, glucose, α-methyl glucoside, polyglucose having an average of about 1 to about 3 glucose residues per molecule, glycerine, pentaerythritol and mixtures thereof, (2) contains an average of from about 10 to about 120, and preferably about 20 to about 80 oxyethylene units; and (3) has an average of about 1 to about 3 fatty acid residues per mole of polyoxyethylene derivative of polyol ester. Examples of such preferred polyoxyethylene derivatives of polyol esters include, but are not limited to PEG-80 sorbitan laurate and Polysorbate 20. PEG-80 sorbitan laurate, which is a sorbitan monoester of lauric acid ethoxylated with an average of about 80 moles of ethylene oxide, is available commercially from ICI Surfactants of Wilmington, Del. under the tradename, "Atlas G-4280." Polysorbate 20, which is the laurate monoester of a mixture of sorbitol and sorbitol anhydrides condensed with approximately 20 moles of ethylene oxide, is available commercially from ICI Surfactants of Wilmington, Del. under the tradename "Tween 20."

The cleansers of the present invention may include one or more glucosides, including, for example, long chain alkyl glucosides or polyglucosides, which are the condensation products of (a) a long chain alcohol containing from about 6 to about 18, and preferably from about 8 to about 14 carbon atoms, with (b) glucose or a glucose-containing polymer. Preferred alkyl gluocosides comprise from about 1 to about 6 glucose residues per molecule of alkyl glucoside. A preferred glucoside is decyl glucoside, which is the condensation product of decyl alcohol with a glucose polymer and is available commercially from Henkel Corporation of Hoboken, N.J. under the tradename, "Plantaren 2000."

Also included in the cleansers of the present invention may be one or more amphoteric surfactants. Examples of amphoteric surfactants suitable for use in the present invention include, but are not limited to, amphocarboxylates such as alkylamphoacetates (mono or di); alkyl betaines; amidoalkyl betaines; amidoalkyl sultaines; amphophosphates; phosphorylated imidazolines such as phosphobetaines and pyrophosphobetaines; carboxyalkyl alkyl polyamines; alkylimino-dipropionates; alkylamphoglycinates (mono or di); alkylamphoproprionates (mono or di),); N-alkyl β-aminoproprionic acids; alkylpolyamino carboxylates; and mixtures thereof.

In one aspect, the cleanser of the present invention may include a combination of PEG 80-SL, an amphoteric surfactant, an alkyl taurate, and decyl glucoside. The PEG 80-SL may be present in an amount of from about 2% to about 6% by weight of the composition, or about 3% to about 4% by weight of the composition. The amphoteric surfactant may be present in an amount of from about 2% to about 6% by weight of the composition, or about 4% to about 5% by weight of the composition. The taurate surfactant may be present in an amount of from about 2% to about 4% by weight of the composition. The decyl glucoside may be present in an amount of from about 1% to about 6% by weight of the composition, or about 3% to about 4% by weight of the composition. In these embodiments, the cleanser desirably does not contain any added conditioning agents, does not contain sulfate-based surfactants, does not contain di-PPG-2 myreth-10 adipate. The cleanser of the present invention is desirably mild, as described below.

Compositions of the present invention may include one or more powdered additives, which are added to the composition to provide a desired texture and deposition onto the skin. For example, powdered additives may include cellulose powders, such as cotton or pulp having an average length of from about 1 to about 1000 μm, a particle aspect ratio from about 1000 to about 2 and a thickness of from about 1 to about 1000 μm. The powdered additives may be hydrophobic, hydrophilic, or combinations thereof, and in some instances has the hydrophobicity or hydrophilicity associated with the powder in its natural state (e.g., not hydrophobically or hydrophobically modified). In one embodiment, the powdered additive may include regenerated cotton, sold under the trade name W325J White Cotton Flock (sold by Solvaira Specialties). Therefore, in some aspects, the composition may provide a desired skin residue value and an after-feel level. The powdered additives may be present in the invention in an amount of from about 0.1% to about 3.0% by weight of the composition, and more desirably about 0.25% to about 1.0% by weight of the composition or about 0.25% by weight of the composition. In some aspects, however, the powdered additive may not be desired and therefore the composition may be free of the powdered additive.

Compositions may include fragrances, including fragrance oils or other fragrant components, or may be free of fragrances. If included, a fragrance may be present in any desired amount, and in some aspects is present from about 0.01% to about 1.0% by weight of the composition. The compositions may also include colorants or dyes, or may be free of dyes or colorants. When used, dyes or colorants may be present in an amount of from about 0.01% to about 1.0% by weight of the composition.

The cleanser may be foamable during use.

Mildness

Since the cleansers are intended to be used on the skin of children, it is desired that the compositions be suitably mild to the skin and eyes. The desired cleanser is considered mild to skin of the child, demonstrating in vitro test scores of Epiderm <150 mg/ml, and MTT cell viability greater than 80%. By way of example, the formulations may be considered mild based upon the mildness test described below:

Mildness Test

Test articles were tested as 10% dilutions (weight-volume percentage [w/v]) in sterile, deionised water (Quality Biological, Gaithersburg, Md., USA) unless otherwise specified. The 10% (w/v) dilution mimics the end-user exposure to wash-off products such as shampoos, conditioners, etc. Sterile, deionised water (Quality Biological, Gaithersburg, Md., USA) was used as the assay negative control.

Reconstructed Tissues

The 3-D human reconstructed epidermal model EpiDerm Skin Model (EPI-200) provided by MatTek Corporation (Ashland, Mass., USA) was used in our experiments. The EpiDerm tissues are based on normal, human-derived epidermal keratinocytes cultured to form a multilayered, highly differentiated model of the human epidermis (20). The EpiDerm tissues were cultured in a Dulbecco's Modified Eagle Medium-based culture medium provided by the tissue manufacturer. Since the tissues have a functional stratum corneum, the test articles were applied directly to the culture surface, at air interface.

Treatment of the EpiDerm Tissues

The EpiDerm tissues were stored at 2-8° C. until used. The day before treatment, the EpiDerm tissues were cultured in six-well plates containing a hydrocortisone free-assay medium (HCF-AM) and equilibrated at 37±1° C. in a humidified atmosphere of 5±1% CO2 in air (standard culture conditions) overnight.

Each EpiDerm tissue was considered an independent sample. At least 16 hours after initiating the tissue cultures, the medium was removed from under the tissues and 0.9 ml of fresh, pre-warmed HCF-AM were added to each well. Each test article (100 µl) was applied onto three tissues, and the negative control (100 µl sterile, deionised $H_2O$) was added to the other three tissues in the six-well plate. At the end of the 1-hour exposure period, each tissue was rinsed five times with approximately 0.5 ml per rinse of calcium- and magnesium-free Dulbecco's phosphate-buffered saline (CMF-DPBS) (Quality Biological). After rinsing, each tissue was placed in the designated well of a new six-well plate containing 0.9 ml of fresh HCF-AM and incubated at standard culture conditions for the post-exposure incubation period (24 hours).

Viability Assay

Tissue viability was determined using a method based on the reduction of the yellow tetrazolium salt 3-(4,5-dimethylthiazol-2-yl)-2,5-diphenyltetrazolium bromide (MTT) to the purple formazan dye by mitochondrial succinate dehydrogenase in viable cells (21). A 1.0-mg/ml solution of MTT in warm MTT addition medium was prepared no more than 2 hours before use.

Upon the completion of the 24-hour post-exposure incubation, the tissues were removed from their incubation medium, rinsed with CMF-DPBS, blotted dry and transferred into pre-labelled 24-well plates containing 300 µl MTT solution per well. The medium remaining from under each tissue was quick-frozen (≤−60° C.) for subsequent cytokine analysis.

After 3±0.1 hours of incubation in MTT, the EpiDerm tissues were blotted on absorbent paper and transferred into 24-well plates containing 2.0 ml of isopropanol per well and shaken at room temperature. After 2 hours, the absorbance of a 200-µl aliquot of tissue extract was measured at 550 nm (Molecular Devices VMax® Kinetic ELISA microplate reader, Sunnyvale, Calif., USA). The viability of the tissues exposed to the test articles was calculated and expressed as a percentage relative to the viability of the negative control-treated tissues. The tissue viability value was taken as the mean value from the three independent wells tested in each experiment.

IL-1α Analysis

The IL-1α concentration was determined using a kit from R&D Systems (Minneapolis, Minn., USA) according to the manufacturer's instructions. Thawed media samples, collected as described previously, were tested neat and as 1:10 dilutions to keep the readings within the linear range of the assay. The IL-1α value reported for each test was the mean value from the three independent tissues used per test article in each experiment and plated in duplicate.

Improved Enjoyment and Non-Functional Aspects

As noted above, the present invention not only facilitates and improves the touch between a caregiver and a child, but also improves the enjoyment and non-functional aspects of giving a child a bath. While the cleansing and "functional" aspect of bathing a child is beneficial, the present invention seeks to use a cleanser and method of cleansing to improve the non-functional aspects of a bath. With a more enjoyable bath experience and the increase in "non-functional" aspects of bath, bonding and social development are increased and improved.

The increased non-functional aspects of bath include one or more of the following: increased eye contact between caregiver and child, increased talking by one or more of the caregiver and child, increased singing by one or more of the caregiver and child, increased tickling or playful touching between caregiver and child, and increased duration and amount of touches by the caregiver to the child's skin. In addition to the increase in the number and/or duration of the non-functional aspects of bathing, the present invention also seeks to provide a cleanser and/or cleansing method that decreases the amount of time spent on functional aspects of bathing (e.g., actual cleansing of skin and/or hair). In some aspects, the invention results in the reduction in functional aspects of bath as compared to a wash with a separate cleanser or without the present method. Further, in some aspects, the present invention results in the amount of functional time during the bathing experience being less than the amount of non-functional time during the bathing experience. In addition, the present invention seeks to reduce the amount or duration of negative vocalizations by the child, such as crying or yelling, during the bathing experience.

The present invention includes a cleanser as described above, but also may include a method of bathing the child. The method is described below. In some aspects of the invention, a product, such as a bottle, may include the cleanser contained therewithin, and also include instructions on the bottle to describe the method described herein. In other aspects, instructions may be provided to a caregiver separately from the bottle, such as in print or online.

The present invention includes methods of improving the bonding between caregiver and child, and/or the social development of a child. The method is directed to improving the non-functional aspects of a bath, including, for example, improving the enjoyment during the bathing experience. As noted above, the exemplary bath to a child is given by a caregiver, such as a parent or guardian, however, other caregivers are included in this method. Further, while the description is directed to a child (e.g., a baby, toddler, or child under age 8), it is understood that bathing may be given to older humans, including those that are incapable of bathing themselves or otherwise require assistance.

In the method, the child is placed into the bathing environment, which may be a tub or other suitable space for cleansing. The caregiver dispenses a desired amount of the cleanser described above into his or her hands, or fingers, or onto a cleansing apparatus, such as a cloth, sponge, loofah, or other cleansing tool, or dispenses a desired amount of cleanser onto the skin of the child. The caregiver then uses his or her fingers or cleansing apparatus to apply and spread the cleanser onto the skin of the child, whereby the application achieves an optimized natural touch. The term "optimized natural touch" is intended to mean one in which the caregiver's touch is not disrupted by the application of product to skin, such that the feel is similar to that of normal skin-to-skin contact, and which is affective in that it includes soft, gentle, and slow touches (e.g., cuddles or tickles). "Optimized touch" is intended to mean the transfer of mechanical forces from the touching finger through the target skin to the nerves and then sensed by the target, where the physical process of touch occurs in a mode close to the natural or unaltered state, where the surface chemistry of the skin, the topography of the target skin, the mechanical properties is not highly altered and that there is not a significant mediating layer on the top of the target skin. For example, if the surface chemistry of the skin is altered such that the friction between finger is skin is lowered the finger will to a greater extent slip over the skin and less contact or touch will be felt. Or if a thin film of residue from a cleansing product is left behind on the skin the film will alter the mechanical transmission of force to the nerves. Or if the skin lipids are highly disordered the mechanical properties of the skin will be changed, in particular the loss modulus will increase, and the transmission of force will be reduced.

The method further includes the caregiver performing one or more actions, including vocalization, such as talking and/or singing. A separate action may include the caregiver bathing by following the lead of the child, which means paying attention to the infant's reactions (e.g., vocalization, gestures, expressions) and responding (e.g., smile back if infant smiles, take a break if infant fusses).

The method described herein promotes child psychological well-being and engagement with the caregiver through the use of the cleanser, which is specifically designed to enhance the perceived experience when the caregiver touches the child. The method additionally provides a benefit of improving and promoting eye contact between the child and caregiver, through the enhanced touch experience. In addition, the present method includes promoting the social and/or emotional development through the improved eye contact and enhanced touch.

With respect to the caregiver specifically, the present invention improves and promotes the caregiver's attention during the bathing interaction by making the bathing process more enjoyable, while reducing stress and anxiety by reducing the slipperiness of skin, and/or increasing the friction between skin so as to improve the ability hold the child safely. It has been found that the present invention improves the happiness and enjoyment of the bathing experience by the child, which has a direct correlation to the happiness and enjoyment of the caregiver. Further, while the caregiver experiences happiness and enjoyment, the caregiver provides enhanced attention and lowered stress, which affect the child.

EXAMPLES

Comparison of Inventive and Commercially Available Washes

Inventive washes were compared to a commercially available wash to determine its impact on the bonding and the bathing experience. The commercially available wash was Aveeno® Baby Soothing Relief Creamy Wash,[1] which was provided to subjects in an overwrapped 8 fl. oz. bottle to blind the product. An accompanying lotion, Aveeno® Baby Soothing Relief Moisture Cream, was also given in an overwrapped 5 fl. oz. bottle. The inventive formula was given in a white 4 fl. oz. bottle. An accompanying lotion was also provided in a plain white bottle to ensure that all mother-infant pairs used the exact same products throughout the study. The inventive product tested had the following formulation:

[1] Aveeno® Baby Soothing Relief Creamy Wash:Water, Coamidopropyl Betaine, Glycerin, Peg-80 Sorbitan Laurate, Sodium Trideceth Sulfate, Acrylates Copolymer, *Avena Sativa* (Oat) Kernel Flour, Sodium Benzoate, Styrene/Acrylates Copolymer, Mineral Oil, Polyquaternium-7, Peg-45M, Benzaldehyde, Sodium Hydroxide, Citric Acid. Aveeno® Baby Soothing Relief Cream: Water, Glycerin, Dimethicone, Distearyldimonium Chloride, Petrolatum, Isopropyl Palmitate, Cetyl Alcohol, *Avena Sativa* (Oat) Kernel Extract, *Avena Sativa* (Oat) Kernel Oil, *Butyrospermum Parkii* (Shea) Butter, Steareth-20, Sodium Chloride, Benzyl Alcohol.

TABLE

| Inventive Formulation | |
|---|---|
| Water | 75.91 |
| Coamidopropyl Betaine | 4.08 |
| Coco-Glucoside/Glyceryl Oleate | 0.35/0.3 |
| Acrylates/C10-30 Alkyl Acrylate Crosspolymer | 0.8 |
| Sodium Benzoate | 0.5 |
| Tetrasodium Glutamate Diacetate | 0.05 |
| PEG-80 sorbitan laurate | 3.24 |
| Decyl glucoside/Lauryl glucoside | 1.26/0.84 |
| Ethylhexylglycerin/Phenoxyethanol | 0.06/0.54 |
| Cotton (powdered) | 0.25 |
| Sodium hydroxide | 0.24 |
| Fragrance | 0.4 |

19 mothers (age 18-35) and 20 infants (including one set of twins; age 0-6 months, full-term meaning ≥37 weeks gestational age) completed this study. All mothers and infants were in good health, and all mothers were a primary caregiver and typical person responsible for bathing their infants. Questionnaire items included ratings on Likert-type agreement scales regarding the bath and activities during the bath as well as the wash products. The Parent-Infant Caregiving Touch Scale (PICTS; Koukounari, Pickles, Hill, & Sharp, 2015) is a composite scale averaging responses on 12 items regarding frequency of engaging in touch behaviors with one's infant over the past two weeks (e.g, cuddle, rock).

At baseline, mothers bathed their infants at the Johnson & Johnson Consumer Experience Center (CXC) in their normal fashion while using the Aveeno® Baby products. The entire bath was recorded and later coded for behaviors and infant responses by expert coders blind to hypotheses using the Facial Action Coding System (FACS). After the bath, mothers applied a commercially available lotion to infant (Aveeno Soothing Relief Moisture Cream) but analyses of bath and lotion-application behaviors and emotions were separate, and data below is only for the bath portion of the study. All mothers then completed a questionnaire. All mothers then viewed a video and were given an informational pamphlet with study instructions about best tips for bath time, and were given a plain, white bottle containing the inventive formula, as well as an accompanying lotion. The most relevant bathing tips recommended setting routines, talking or singing to baby during bath, recommended spending more time touching the baby, and following the baby's lead. Mothers were instructed to bathe their child at least three times per week for the next two weeks using the inventive product. Two weeks after baseline, all mothers returned to the CXC and once again bathed their children using the inventive product, and again were recorded and completed a questionnaire. Videos were again coded using FACS.

Results:

On average, mothers bathed their infants 4.5 times per week at home using the inventive product. Self-report from the questionnaires and coded behaviors from the videos were compared. All behaviors were coded only from the portions of the videos while the infants were in the bath. Overall, results revealed that the inventive product led to a more emotional bath with a better sensory touch experience and other interactions between mother and baby that are related to long-term bonding and development. Coded behaviors from the baseline bath compared to the inventive bath showed that the inventive bath resulted in mothers spending a greater proportion of the bath time talking or singing, making eye-contact with their babies, more non-functional, playful touch (tickling), and less time doing functional activities such as washing their baby. Video coding also determined that that infants responded more to the inventive formula bath, in that they made more eye-contact and engaged in less negative vocalizations (e.g., crying).

Mothers also self-reported on the questionnaires that the bath using the inventive formula resulted in better outcomes. Similar to the behavioral coding, mothers reported that they engaged in more eye-contact and talking and singing, as well as more and better quality touch with their infants. Specifically, they reported that the inventive formula enhanced the sensory experience of touch between them and their babies and encouraged more touch. The PICTS scores also suggested that mother were generally engaging in more touch during the time they used the inventive formula. The results from the first bath (taken with the commercially available product) and the inventive bath (taken with the inventive product), are set forth in the Table below.

TABLE

Results

|  | Control Bath | Inventive Bath |
|---|---|---|
| Caregiver Talking or singing (% of bath time) | 45.3% | 52.4% |
| Caregiver making eye-contact with baby (% of bath time) | 28.0% | 57.4% |
| Functional: Washing baby (% of bath time) | 31.4% | 22.9% |
| Caregiver tickles baby (mean count) | 0.10 | 0.85 |
| Baby making eye-contact with caregiver (% of bath time) | 14.3% | 18.0% |
| Baby Negative vocalizations (% of bath time) | 9.2% | 6.5% |

Further, the self-reporting questionnaires demonstrated an improvement with the inventive product as compared to the commercially available product. The self-reporting scores (based on a score of 1-5, with 1 being the lowest and 5 being the highest score), are set forth below in the Tables below.

TABLE

Self-reporting

| (Scale 1-5) | Control | Inventive |
|---|---|---|
| I talked or sang to my baby during bath time | 4.68 | 4.95 |
| My baby and I made eye-contact during bath time | 4.47 | 4.74 |

TABLE

Self-reporting - Touch

| (Scale 1-5) | Control | Inventive |
|---|---|---|
| These products enhance the sensory experience of touch between mom and baby | 4.32 | 4.84 |
| These products encourage touch between mom and baby | 4.42 | 4.84 |
| Parent-Infant Caregiving Touch Scale (0-4 scale) | 3.1 | 3.3 |

As can be seen from the results above, the objective results show a marked improvement in a number of factors the demonstrate enjoyment, bonding, and happiness during the bath when the inventive product was used as compared to the commercially available product. The self-reporting scores also demonstrate a marked improvement in all areas that are associated with enjoyment, bonding and happiness.

Further, and perhaps most surprisingly, the inventive product also demonstrated a significant reduction in the amount of functional time (e.g., washing the baby). This demonstrates that the inventive product is helpful in not only the act of cleansing, but also the non-functional actions that are associated with an enjoyable and developmental bath. By focusing less on the cleansing, and more on the enjoyment and fun associated with the bath, the mothers using the inventive product were able to bond and play with their baby more.

The inventive product therefore has been found to be a useful tool to achieve happiness, enjoyment, and social behaviors when used in a bath setting. Further, the inventive product was also found to drive the mother to perform less "functional" actions during bath and focus more on the bonding and social actions associated with bath time.

The invention claimed is:
1. A method of improving the experience of bath time, comprising employing a cleanser that promotes good skin-to-skin contact between caregiver and child,
    wherein the cleanser comprises PEG 80-SL, an amphoteric surfactant, an alkyl taurate, and decyl glucoside.

* * * * *